United States Patent
Wang et al.

(10) Patent No.: US 7,682,838 B2
(45) Date of Patent: Mar. 23, 2010

(54) MAGNETIC NANOPARTICLES, MAGNETIC DETECTOR ARRAYS, AND METHODS FOR THEIR USE IN DETECTING BIOLOGICAL MOLECULES

(75) Inventors: Shan X. Wang, Portola Valley, CA (US); Robert L. White, Stanford, CA (US); Chris D. Webb, Scotts Valley, CA (US); Guanxiong Li, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 124 days.

(21) Appl. No.: 11/938,187

(22) Filed: Nov. 9, 2007

(65) Prior Publication Data

US 2008/0255006 A1 Oct. 16, 2008

Related U.S. Application Data

(62) Division of application No. 10/829,505, filed on Apr. 22, 2004.

(60) Provisional application No. 60/519,378, filed on Nov. 12, 2003.

(51) Int. Cl.
*G01N 33/543* (2006.01)
*G01N 1/36* (2006.01)

(52) U.S. Cl. .............. 436/526; 436/518; 422/50; 422/98; 422/276; 365/173; 209/214; 210/222; 210/223

(58) Field of Classification Search ........... 436/526, 436/518; 422/50, 98, 276; 365/173; 209/214; 210/222, 223
See application file for complete search history.

(56) References Cited

U.S. PATENT DOCUMENTS

| 5,650,958 | A | * | 7/1997 | Gallagher et al. | ........... 365/173 |
| 5,981,297 | A | | 11/1999 | Baselt | |
| 6,323,634 | B1 | | 11/2001 | Naakagawa et al. | |
| 6,468,809 | B1 | * | 10/2002 | Prinz et al. | ........... 436/526 |
| 6,582,921 | B2 | | 6/2003 | Mirkin et al. | |

(Continued)

FOREIGN PATENT DOCUMENTS

WO 01/14591 3/2001

(Continued)

OTHER PUBLICATIONS

Baselt, D.R., et al.; "A Biosensor Based on Magnetoresistance Technology," Biosensors and Bioelectronics, vol. 13, issues 7-8, Oct. 1998, pp. 731-739.

(Continued)

*Primary Examiner*—Mark L Shibuya
*Assistant Examiner*—Pensee T Do
(74) *Attorney, Agent, or Firm*—Bozicevic, Field & Francis LLP; Bret E. Field

(57) ABSTRACT

Magnetic nanoparticles and methods for their use in detecting biological molecules are disclosed. The magnetic nanoparticles can be attached to nucleic acid molecules, which are then captured by a complementary sequence attached to a detector, such as a spin valve detector or a magnetic tunnel junction detector. The detection of the bound magnetic nanoparticle can be achieved with high specificity and sensitivity.

9 Claims, 6 Drawing Sheets

U.S. PATENT DOCUMENTS

| | | | |
|---|---|---|---|
| 6,623,983 | B1 | 9/2003 | Terstappen et al. |
| 6,764,861 | B2 * | 7/2004 | Prinz et al. .................. 436/526 |
| 2002/0060565 | A1 | 5/2002 | Tondra |
| 2005/0025969 | A1 | 2/2005 | Berning et al. |

FOREIGN PATENT DOCUMENTS

| | | |
|---|---|---|
| WO | 01/57506 | 8/2001 |
| WO | 03/054523 | 7/2003 |

OTHER PUBLICATIONS

Miller, M. M., et al.; "A DNA Array Sensor Utilizing Magnetic Microbeads and Magnetoelectronic Detection," Journal of Magnetism and Magnetic Materials; 225, pp. 138-144 (2001).

Graham, D. L., et al.; "Single Magnetic Microsphere Placement and Detection on-chip Using Current Line Designs with Integrated Spin Valve Sensors: Biotechnological Applications;" J. Appl. Phys., 91: 7786 (2002).

Sun, S.; Murray, C.B.; "Synthesis of Monodisperse Cobalt Nanocrystals and their Assembly into Magnetic Superlattices," J. Appl. Phys., 85: 4325 (1990).

Parkin, S. S. P., et al. "Oscillations in Exchange Coupling and Magnetoresistance in Metallic Superlattice Structures: CoJRu, ColCr, and FelCr;" Phys. Rev. Lett., 64(19) 2304, (1990).

Slonczewski, John C., et al.; "Micromagnetics of Laminated Permalloy Films:" IEEE Trans. Magn., 24(3): pp. 2045-2054; (1998).

Li, G. et al.; "Detection of Single Micron-Sized Magnetic Bead and Magnetic Nanoparticles Using Spin Valve Sensors for Biological Applications;" J. Appl. Phys., 93(10): pp. 7557-7559 (2003).

Parkin, S.S.P. et al.; Exchange-Biased Magnetic Tunnel Junctions and Application to Nonvolatile Magnetic Random Access Memory (Invited); J. Appl. Phys., 85(8): pp. 5828-5833 (1999).

van de Veerdonk, R.J.M., et al., "Current Distribution Effects in Magnetoresistive Tunnel Junctions;" Appl. Phys. Lett., 71 (19): pp. 2839-2841 (1997).

Li, G., et al.; "Analytical and Micromagnetic Modeling for Detection of a Single Magnetic Microbead or Nanobead by Spin Valve Sensors;" IEEE Trans. Magn., 39 (5): pp. 3313-3315 (2003).

Thorsen, T., et al., "Microfluidic Large-Scale Integration;" Science,vol. 298, pp. 580-584 (2002).

Tehrani, S., et al.; "Recent Developments in Magnetic Tunnel Junction MRAM;" IEEE Trans. Magn., vol. 36 (5); pp. 2752-2757, (2000).

Sun, S., et al.; "Polymer Mediated Self-Assembly of Magnetic Nanoparticles;" J. Am. Chem. SOC., vol. 124 (12); pp. 2884-2885, (2002).

Sellmyer, D.J., et al; 'Handbook of Thin Film Materials,' Edited by: Nalwa, H.S., Stanford Scientific Corporation; Academic Press, vol. 5; pp. 337-374 (2002).

C.B. Murray, et al., MRS Bulletin, vol. 26(12): pp. 985-991, (2001).

Bozorth, R.M., "Fe~omagnetism," D. Van Nostrand Company, Inc. pp. 190-209 (1951).

M. Schena, R.W. Davis, Mcroarray Biochip Technology, Eaton Publishing, pp. 1-18 (2000).

Lagae L. et al., "On-chip manipulation and magnetization assessment of magnetic bead ensembles by integrated spin-valve sensors", Journal of Applied Physics, May 15, 2002, vol. 91, No. 10, pp. 7445-7447, XP012054843, ISSN: 0021-6979.

Ferreira H. A. et al., "Detection of bimolecular recognition using nanorneter-sized magnetic labels and spin-valve sensors", Digest of Intermag 2003, IEEE International Magnetics Conference: Mar. 28, 2003, pp. EC-4, XP010685265, ISBN: 0-7803-7647-1.

Wang S. X. et al., "Design and fabrication of bio-magnetic sensors and magnetic nanobead labels for dna detection and identification", Digest of Intermag 2003, IEEE International Magnetics Conference, Mar. 28, 2003, pp. EC-1, XP01066526, ISBN: 0-7803-7647-1.

Graham D. L. et al., "High sensitivity detection of molecular recognition using magnetically labelled biomolecules and magnetoresistive sensors", Biosensors and Bioelectronics, Apr. 1, 2003, vol. 18, No. 4, pp. 483-488, XP002429396.

Ferreira H. A. et al., "Biodetection using magnetically labeled biomolecules and arrays of spin valve sensors (invited)", Journal of Applied Physics, May 15, 2003, vol. 93, No. 10, pp. 7281-7286, XP012058127, ISSN: 0021-8979.

Freitas P. P. et al., "Magnetoresistive biochips", Europhysics News, Nov. 2003, vol. 34, No. 6, pp. 224-226, XP002429397, ISSN: 0531-7479.

* cited by examiner (a) Long detector     detectors     (b) Short detector

MAGNETIC NANOPARTICLES, MAGNETIC DETECTOR ARRAYS, AND METHODS FOR THEIR USE IN DETECTING BIOLOGICAL MOLECULES

CROSS REFERENCE TO RELATED APPLICATIONS

The present application is a Divisional Application of U.S. patent application Ser. No. 10/829,505, filed Apr. 22, 2004, which claims priority to U.S. Provisional Patent Application Ser. No. 60/519,378, filed Nov. 12, 2003, the contents of which are incorporated herein by reference.

STATEMENT REGARDING FEDERALLY SPONSORED RESEARCH OR DEVELOPMENT

The government may own rights in the present invention pursuant to grant number N00014-02-1-0807 from the U.S. Defense Advanced Research Projects Agency (DARPA).

FIELD OF THE INVENTION

The invention relates to magnetic nanoparticles, magnetic nanoparticle detectors, and methods of detecting biological materials, whether natural or synthetic, and whether modified or unmodified. The invention also relates to the magnetic nanoparticle materials for use in detecting biological materials, and methods for making those materials. Finally, the invention relates to magnetic particle detectors and related apparatus, as well as methods of using such apparatus for the detection of biological materials.

DESCRIPTION OF RELATED ART

The development of high sensitivity, quantitative DNA fragment detection and identification systems has been of growing importance in the fields of functional genomics, forensics, bio-defense, anti-bioterrorism, and other biotechnology applications.

Ideally, detection systems should be sensitive, rapid, portable, inexpensive, and reusable. Additionally, it is preferable that the systems do not require DNA amplification processes such as the polymerase chain reaction (PCR). More specifically, the system should preferably have the following characteristics: (1) one DNA fragment per tag, (2) each tag is individually detectable, (3) an effectively infinite number of detectors, and (4) known efficiency of the attachment processes involved. Currently, no system is commercially available that satisfies all of these requirements.

Numerous of the current microarray systems utilizing fluorescent labeling (tagging) are inherently of low sensitivity because they require approximately $10^4$ molecules to achieve a useful signal to noise ratio (thereby violating the ability to have each tag be individually detectable) and are only marginally quantitative because of the optical systems involved, crosstalk, and bleaching (M. Schena, R. W. Davis, *Microarray Biochip Technology*, Eaton Publishing, pp. 1-18 (2000)). Further, the optical detection systems are usually used in conjunction with the polymerase chain reaction (PCR).

However, several groups have recently taken a new approach to detecting target molecules. In U.S. Pat. No. 5,981,297 to Baselt (issued Nov. 9, 1999), a group at the Naval Research laboratory offered both an apparatus and methods for detecting target molecules using a magnetoresistive or magnetostrictive magnetic field sensor having binding molecules attached which are reported to selectively bind target molecular species, which in turn are attached to paramagnetic polymer beads.

In a related published article by D. R. Baselt, et al., entitled "A Biosensor Based on Magnetoresistance Technology", (*Biosensors and Bioelectronics*, Vol. 13, no. 7-8: 731-739 (1998)), a magnetic detection system which they called BARC (Bead Array Counter) is offered. According to the article, the BARC measures the forces that bind molecules such as DNA together, and use these interactions to hold magnetic microbeads to a solid substrate. Microfabricated magnetoresistive transducers on the substrate are reported to indicate whether the beads are removed when pulled by magnetic forces, and can be adapted to chips for use in multi-analyte detection capabilities.

M. M. Miller, et al., ("A DNA Array Sensor Utilizing Magnetic Microbeads and Magnetoelectronic Detection", *Journal of Magnetism and Magnetic Materials*, 225: 138-144 (2001)) offers a multi-analyte biosensor that uses magnetic microbeads as labels to detect DNA hybridization on a microfabricated chip. The beads are detected using giant magnetoresistance magnetoelectronic sensors that are embedded in the chip itself, allowing for the simultaneous detection of eight different analytes.

In U.S. patent application Ser. No. 2002/0060565 (published May 23, 2002), Tondra suggests a ferromagnetic, thin-film based magnetic field detection system useful in detecting the presence of selected molecular species. According to the specification of this patent application, a magnetic field sensor is supported on a substrate that has a binding molecule layer positioned on a side of the substrate and is capable of selectively binding to the selected molecular species.

Finally, a group in Portugal has deployed spin valve sensors coupled with coils at proximity (D. L. Graham, et al., *J. Appl. Phys.*, 91: 7786 (2002)). The magnetic tags used were about 2 μm in diameter for the paramagnetic polystyrene balls, and similarly sized for the ferromagnetic particles. The larger tags were coupled to a much larger and not easily ascertainable number of DNA fragments, prejudicing the quantitative capabilities of the system. The dimensions of the tags and of the magnetic detector suggested in this paper limit the detector density to levels $10^2$ to $10^4$ less than the approach disclosed herein.

Despite the advances achieved so far, there still remains a need for detection systems which ideally meet all four desirable qualities listed above.

SUMMARY OF THE INVENTION

A system of magnetic nanoparticles and detector arrays are described. The system is useful for the high-sensitivity detection of nucleic acid molecules such as DNA. The nanoparticles can be high moment magnetic nanoparticles that are superparamagnetic, or antiferromagnetic nanoparticles which contain at least two layers of antiferromagnetically-coupled high moment ferromagnets.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

DEFINITIONS

The following definitions are provided in order to aid those skilled in the art in understanding the detailed description of the present invention.

"Binding molecule", as used herein, refer to antibodies, strands of polynucleic acids (DNA or RNA), and molecular receptors capable of selectively binding to or 'recognizing' potential target molecules such as polynucleic acids, enzymes, proteins, peptides, antibodies, lipids, polymers, metal ions, and low molecular weight organic and inorganic species such as toxins, drugs (both prescription and illicit), explosives, and biohazards.

"Target molecule", or "target species", as used herein, refers to the molecule, molecular species, or organism whose presence, absence, or concentration the assay in question actually determines. Target molecules included for use with the present invention include but are not limited to viruses, bacteria, other biological organisms such as fungi, antibodies, proteins, peptides, polynucleic acids, lipids, polymers, pharmaceutical compounds, organic compounds, biohazardous compounds, explosive compounds, and toxins, among others.

"Detector", as used herein, refers to any number of magnetic detection systems including spin valve detectors (also referred to as spin valve film detectors), magnetic tunnel junction (MTJ) detectors, and MagArray™ detectors, as well as MagArray™ variants of both spin valve detectors and MTJ detectors.

DETAILED DESCRIPTION OF THE INVENTION

Figure 1:
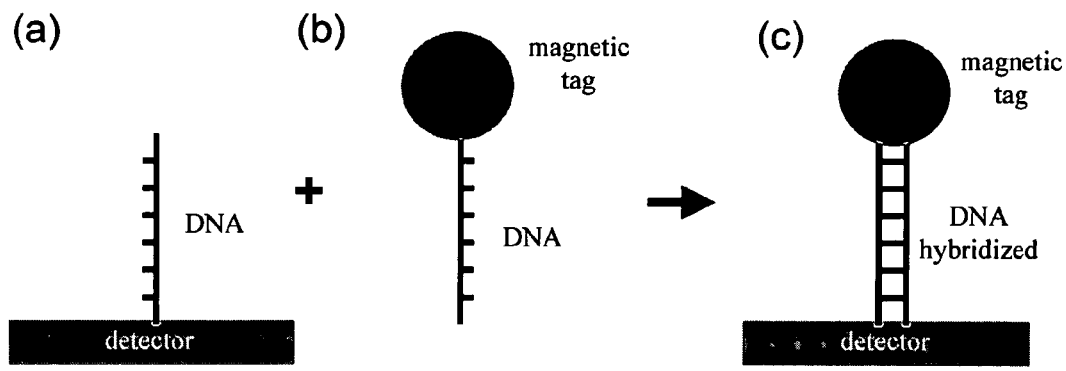
FIG. 1A shows a schematic of a DNA detector comprised of a DNA probe (binding molecule) and a spin valve or magnetic tunnel junction (MTJ) detector, in accordance with one aspect of the present invention.
FIG. 1B shows a magnetic nanoparticle tag attached to a DNA fragment to be detected (target molecule).
FIG. 1C shows the configuration of the DNA detector and the magnetic nanoparticle tag after the target DNA and binding DNA are hybridized.
Figure 2A:
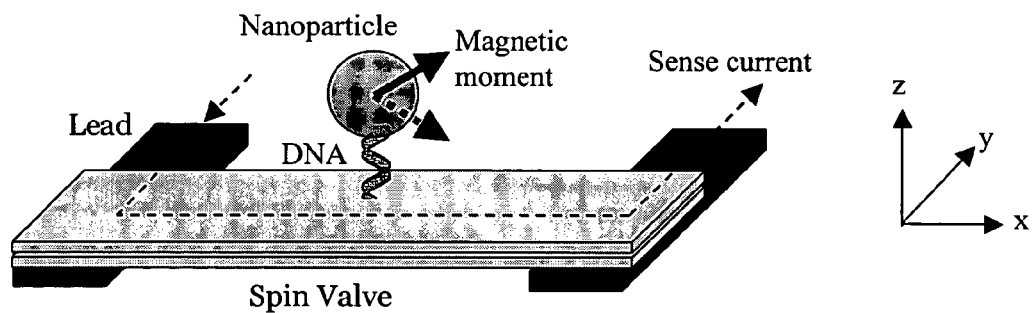
FIG. 2A shows a spin valve detector with a magnetic tag above it, illustrating the pinned layer magnetization along the y-direction. The free layer magnetization has an easy-axis along x and hard-axis along y.
Figure 2B:
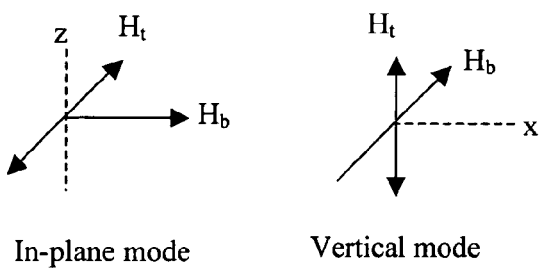
FIG. 2B shows two modes of interrogation method of spin valve detector, the AC tickling field $H_t$ is either parallel (in-plane mode) or normal to (vertical mode) the spin valve plane (x-y plane). $H_b$ is the DC bias field.
Figure 2C:
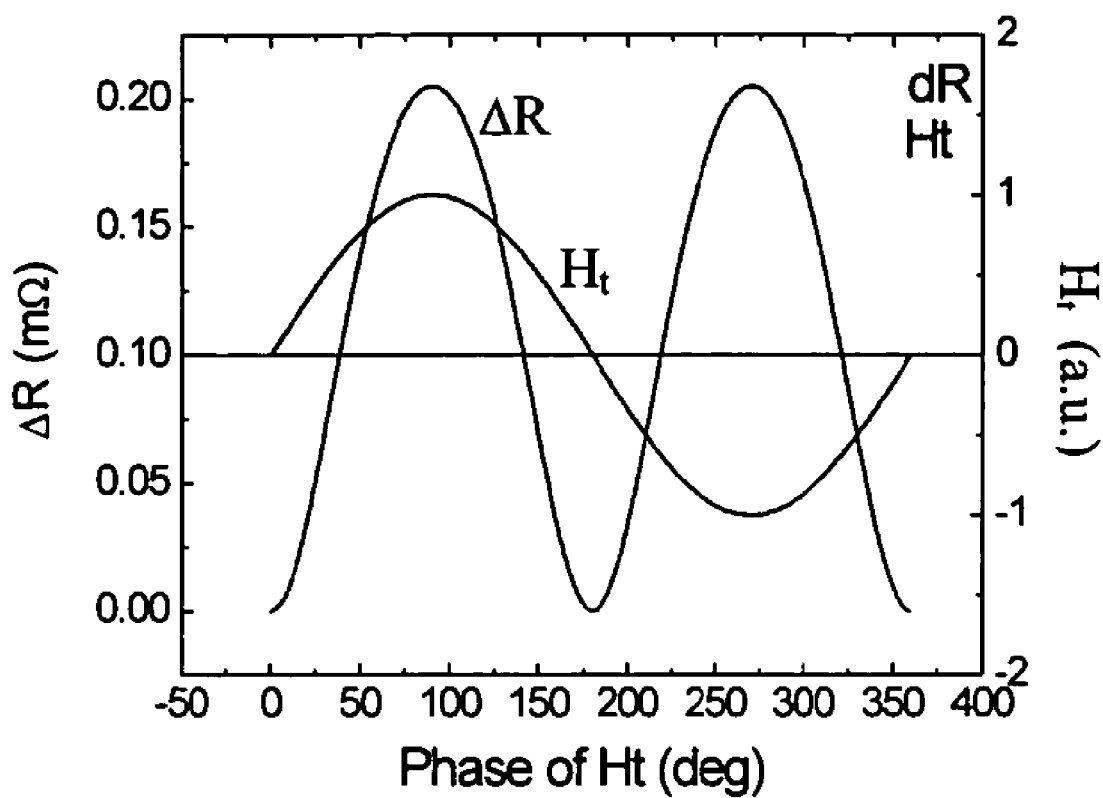
FIG. 2C shows spin valve resistance change $\Delta R$ due to a single Co nanoparticle as a function of the phase of the tickling field $H_t$ in the vertical detection mode.

A detection system can typically involve an array of spin valves or MTJ detectors, oligonucleotide probes complementary to a target of interest attached to individual detectors in the array as shown in FIG. 1A, a macrofluidic or microfluidic sample delivery system, and magnetic nanoparticles bound with target DNA fragments as shown in FIG. 1B. Tagged DNA fragments are delivered by fluidic channels to the detector array for selective hybridization as shown in FIG. 1C. Non-hybridized DNA fragments are washed away, or are removed by a magnetic field gradient. The detector array is interrogated with a combination of DC bias field and AC tickling field, as shown in FIGS. 2A and 2B. The applied fields cause the magnetic nanoparticle tags to display net magnetic moments, which in turn can be picked up by the spin valve or MTJ detectors. In the in-plane detection mode, the detector signal has the same frequency as the AC tickling field $H_t$. In contrast, in the vertical mode, the detector signal is a second harmonic of the AC tickling field as shown in FIG. 2C. In either case, lock-in detection can be employed even if the signal to noise ratio is small. The presence of a magnetic nanoparticle tag, signaling the presence of a target DNA fragment, can thus be detected. The detector voltage signal is proportional to the number of magnetic nanoparticles, and therefore the number of target DNA fragments.

Generally, a DNA fragment can be tagged with a magnetic nanoparticle. The tagged fragment can be selectively bound to a substrate using a complementary nucleotide above a spin valve. The spin valve is then used to detect the magnetic nanoparticle.

The methods and systems disclosed herein are much more sensitive than the previously reported optical detection systems and the other magnetic detection schemes of the known prior art. The inventive systems are more efficient and sensitive than BARC, since they involve spin valve or MTJ detector designs. Additionally, nanometer-scale particles of high magnetic moment are used as biomolecule tags instead of larger particles with more dilute magnetic material. The systems are more sensitive than functional MRI (fMRI) systems. Calculations indicate that the amount of gadolinium required for detection by fMRI far exceeds the amount of magnetic nanotags that can be detected with the inventive systems. Finally, the inventive systems do not require the sophisticated cooling apparatuses required for detection by SQUID (Superconducting Quantum Interference Device) detector systems.

Aspects of the invention include magnetic nanoparticles, detectors, detection systems, and methods for their use. Various aspects of the invention are discussed below. U.S. Trademark application Ser. No. 78285336 was filed on Aug. 9, 2003 for the mark MAGARRAY (Applicant Sunrise Associates).

Nanoparticles

Nanoparticles useful in the practice of the present invention are preferably magnetic (i.e., ferromagnetic) colloidal materials and particles. The magnetic nanoparticles can be high moment magnetic nanoparticles which are small in size so as to be superparamagnetic, or synthetic antiferromagnetic nanoparticles which contain at least two layers of antiferromagnetically-coupled high moment ferromagnets. Both types of nanoparticles appear "nonmagnetic" in the absence of magnetic field, and do not normally agglomerate. In accordance with the present invention, magnetizable nanoparticles suitable for use comprise one or more materials selected from the group consisting of paramagnetic, superparamagnetic, ferromagnetic, and ferrimagnetic materials, as well as combinations thereof.

The magnetic nanoparticles preferably possess the following properties: (1) their remnant magnetization is as small as possible so that they preferably will not agglomerate in solutions (either superparamagnetic particles or antiferromagnetic particles can satisfy this requirement); (2) the tags display high magnetic moments under a modest magnetic field of about 100 Oe so they can be readily detected; (3) the size of the tags preferably is comparable to the target biomolecules so that they do not interfere with the DNA hybridization process and other biological processes; (4) the tags preferably are uniform and chemically stable in a biological environment; and/or (5) the tags preferably are biocompatible, i.e., water soluble and functionalized so that they are readily attached to DNA fragments or other biomolecules.

The nanoparticles are preferably high moment magnetic nanoparticles such as Co, Fe or CoFe nanocrystals which are superparamagnetic at room temperature. They can be fabricated by chemical routes such as salt reduction or compound decomposition in appropriate solutions. Examples of such magnetic nanoparticles have been published in the literature (S. Sun, and C. B. Murray, *J Appl. Phys.*, 85: 4325 (1999); C. B. Murray, et al., *MRS Bulletin*, 26: 985 (2001)). These particles can be synthesized with controlled size (e.g., 5-12 nm), are monodisperse, and are stabilized with oleic acid. In accordance with the present invention, it is also possible to fabricate high magnetic moment nanoparticles in a nanocluster deposition system (D. J. Sellmyer, et al., Chap. 7, Handbook of Thin Film Materials, edited by H. S. Nalwa, Academic Press (2002)). These particles have been developed for applications in bioconjugation. Magnetic nanoparticles and nanopowders suitable for use with the present invention include but are not limited to Co, Co alloys, ferrites, Cobalt nitride, Cobalt oxide, Co—Pd, Co—Pt, Iron, Iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, and Ni alloys. Alternatively and equally acceptable, a thin layer of gold can be plated onto a magnetic core, or a poly-L-lysine coated glass surface can be attached to a magnetic core. Suitable nanoparticles are commercially available from, e.g., Nanoprobes, Inc. (Northbrook, Ill.), and Reade Advanced Materials (Providence, R.I.).

Magnetic nanoparticle tags can be fabricated by physical methods instead of chemical routes, and are suitable for labeling the target biomolecules to be detected. The tags comprise at least two thin ferromagnetic layers, preferably $Fe_xCo_{1-x}$, wherein x is 0.5 to 0.7, or $Fe_xCo_{1-x}$ based alloys. $Fe_xCo_{1-x}$ has the highest saturation magnetization (about 24.5 kGauss) among the known ferromagnetic materials (R. M. Bozorth, Ferromagnetism, D. Van Nostrand Company (1951)). These ferromagnetic layers are separated by nonmagnetic spacer layers such as Ru, Cr, Au, etc., or their alloys. The spacer layers are appropriately engineered to make the ferromagnetic layers coupled antiferromagnetically so that the net remnant magnetization of the resulting particles are zero or near zero. The antiferromagnetic coupling can be achieved via RKKY exchange interaction (S. S. P. Parkin, et al., *Phys. Rev. Lett.*, 64 (19): 2304 (1990)) and magnetostatic interaction (J. C. Slonczewski, et al., *IEEE Trans. Magn.*, 24 (3): 2045 (1988)) as practiced in the magnetic data storage industry. However, the antiferromagnetic coupling strength preferably is moderate so that the particles can be saturated (i.e., magnetization of all layers become parallel) by an external magnetic field of about 100 Oe. This can be achieved by adjusting layer thicknesses and by alloying the spacer layer.

To facilitate the bio-conjugation of the nanoparticle, a gold cap can be added at the top of the antiferromagnetic stack so that the nanoparticle can be conjugated to biomolecules via the gold-thiol linkage. Furthermore, appropriate surfactants can also be readily imparted to the nanoparticles, rendering them water-soluble. The edge of the nanoparticles can be passivated for chemical stability with Au or other thin inert layers.

Many physical methods can be conceived by those familiar with the art to fabricate the nanoparticles described above. A film stack can be made of nanometer-scale ferromagnetic and spacer layers, so they need to be deposited on ultrasmooth substrates (or release layer). The mask layer can be formed by imprinting, etching, self assembly, etc. Subsequently the mask layer and unwanted film stack are removed and cleaned off thoroughly. Then, the release layer is removed, lifting off nanoparticles which are the negative image of the mask layer. These particles are eventually imparted with surfactants and biomolecules. The ultrasmooth substrate can be reused after thorough cleaning and chemical mechanical polishing (CMP).

Alternatively, the nanoparticles can be fabricated with a subtractive fabrication method. In this case, the film stack is directly deposited on the release layer followed by a mask layer. The film stack is etched through the mask layer, and eventually released from the substrate. These nanoparticles result from a positive image of the mask layer as opposed to the case in the additive fabrication method.

The size of the magnetic nanoparticles suitable for use with the present invention is preferably comparable to the size of the target biomolecule to be worked with, such that the nanoparticles do not interfere with biological processes such as DNA hybridization. Consequently, the size of the magnetic nanoparticles is preferably from about 5 nm to about 250 nm (mean diameter), more preferably from about 5 nm to about 150 nm, and most preferably from about 5 nm to about 20 nm. For example, magnetic nanoparticles having a mean diameter of 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, and 150 nm, as well as nanoparticles having mean diameters in ranges between any two of these values, are suitable for use with the present invention. Further, in addition to the more common spherical shape of magnetic nanoparticles, nanoparticles suitable for use with the present invention can be disks, rods, coils, or fibers.

Synthetic antiferromagnetic nanoparticles for use in this application may be considerably larger than ordinary ferromagnetic particles. This is because, to prevent clumping, the nanoparticle must have no net magnetic moment (or a very small magnetic moment) in zero applied field. Antiferromagnetic particles may have zero magnetic moment in zero field at all sizes, but for a ferromagnetic particle its size must be below the "superparamagnetic limit", which is typically 20 nm or less, usually less. To demonstrate the advantage of the synthetic antiferromagnetic particle we have made a calculation of the voltage produced in a spin valve detector for a synthetic antiferromagnetic particle 30 nm in diameter and 30 nm in height and compared it to the voltages produced by 16 nm diameter $Fe_3O_4$ and 11 nm diameter Co nanoparticles. We assume that 75% of the synthetic antiferromagnetic particle is ferromagnetic FeCo and that the spin valve detector is the same in all cases. Table 1 gives the results of these calculations and the caption of Table 1 gives the spin valve dimensions and operating conditions. Note that the spin valve signal from the synthetic antiferromagnet is nearly two orders of magnitude greater than for the ferromagnetic particles.

TABLE 1

Spin valve signal voltage (peak-to-peak amplitude) versus magnetic tag. Only the data for the vertical detection mode (FIG. 2B) is listed here. The voltage is due to a single nanoparticle with its center 20 nm away from the midplane of the spin valve free layer. The sensor size is 3 μm × 0.2 μm with an active length of 1 μm. The sense current density is $10^8$ A/cm$^2$. The effect of the stray field from the spin valve sensor is included in the calculation. The synthetic FeCo is assumed to saturate at 30 Oe and the particle physically rotates with the applied field. Note that the room temperature magnetic moments of the superparamagnetic nanoparticles are reduced as described by the Langevin function, but that of the synthetic antiferromagnetically coupled nanoparticles is changed much less by superparamagnetism.

| Particle | Synthetic FeCo | $Fe_3O_4$ | Co |
| --- | --- | --- | --- |
| Saturation magnetization | 1950 emu/cc | 480 emu/cc | 1400 emu/cc |
| Size | 30 nm diameter, 30 nm height | 16 nm diameter | 11 nm diameter |
| Net saturation moment | 31 femtoemu @ 75 vol % magnetic | 1.0 femtoemu @ 100 vol % | 1.0 femtoemu @ 100 vol % |
| Vertical mode SV detector signal (bias field 100 Oe, tickling field 141 Oe) | 193 μV | 0.9 μV | 0.8 μV |

Note that the signal levels listed in Table 1 are for spin valve detectors. If replaced with an MTJ detector with a junction area of 0.2 μm by 0.2 μm and resistance-area product of 1 kOhm-μm$^2$, operating with a magnetoresistance (MR) of 25% at a bias voltage of 250 mV, and $H_b$=35 Oe, $H_t$=100 Oe rms, the voltage signal from a single synthetic FeCo nanoparticle could reach greater than 1 mV. This signal level makes it detectable without a lock-in amplifier, greatly speeding up the entire MagArray™ detector readout process.

In addition to their advantageous signal level, the synthetic antiferromagnetically coupled nanoparticles can be saturated in different applied fields. This feature can be exploited for multiplex magnetic separation of cells. For the MagArray™ detector, different kinds of synthetic antiferromagnetically coupled nanoparticles with a series of saturation threshold fields can be used to label the biomolecules from different biological processes, thus achieving multiplex biological analysis such as "multi-color" gene expression analysis. For example, consider a "two-color" gene expression scheme with two types of magnetic particles, one saturating in 100 Oe and the other in 125 Oe. We can then interrogate the MagArray™ detector with a two-test sequence. The first test saturates the first type of magnetic particles and gives a voltage signal $V_1$, then the second test saturates both types of magnetic particles and gives a voltage signal $V_2$. Both types of particles contribute to the signals measured in the tests. If the numbers of the two types of particles at a given site are $N_1$ and $N_2$, respectively, then the tested voltage signals should be:

$$V_1 = \alpha_{11} \times N_1 + \alpha_{12} \times N_2,$$

$$V_2 = \alpha_{21} \times N_1 + \alpha_{22} \times N_2,$$

where $\alpha_{ij}$ (ij=11, 12, 21, or 22) are calibration constants. By solving the above equations, we can quantify both types of particles and the two types of genes (or other biomolecules) tagged to them.

The synthetic nanoparticles described above can be produced in large quantities using a large wafer and standard vacuum thin film deposition processes. For example, with a 6-inch round wafer, we can produce 30-nm diameter nanoparticles at a rate of roughly $5 \times 10^{12}$ particles per run, assuming each particle occupies a square of 60 nm by 60 nm on the wafer.

High Sensitivity Spin Valve Detectors

A spin valve detector is a metallic multilayer thin-film structure of two ferromagnetic layers spaced by a non-magnetic layer such as copper. One ferromagnetic layer, called the pinned layer, has its magnetization pinned to a certain direction, while the magnetization of the other ferromagnetic layer, called the free layer, can rotate freely under an applied magnetic field. The electrical resistance of a spin valve depends on the relative orientation of magnetization of the free layer to that of the pinned layer. When the two magnetizations are parallel, the resistance is the lowest; when anti-parallel, the resistance is the highest. The relative change of resistance is called the magnetoresistance (MR) ratio. The MR ratio of a spin valve can reach more than 10% in a small magnetic field, e.g., 100 Oe. Therefore, a spin valve is a good sense element for the detection of a small magnetic particle that is attached to a DNA fragment as a label and immobilized onto the sensor surface. Since the particle is magnetic (under a DC bias field), it generates a magnetic field. The magnetic field may then affect the orientation of the free layer magnetization, causing a change in the electrical resistance of the spin valve.

The operation of a spin valve detector (FIGS. 2A and 2B) is described as follows: 1) The magnetic nanoparticle under a DC bias field ($H_b$) generates a magnetic field around it. 2) The magnetic field will affect the resistance of a spin valve closely underneath it. 3) Application of an AC tickling field ($H_t$) will force the moment of particle to oscillate, resulting in an oscillating MR signal from spin valve. Note that in the in-plane mode the spin valve detector signal due to the magnetic nanoparticle has the same frequency f as the AC tickling field $H_t$, while in the vertical mode the signal has twice the frequency of $H_t$. 4) A lock-in amplifier is used to pick up such an oscillating signal with a high signal-to-noise ratio.

Spin valves have a magnetoresistive (MR) ratio of typically 5-12% and are used in hard disk drives to detect a magnetic bit made of only a few hundred closely packed Co alloy nanoparticles (size is about 10 nm) with a signal to noise ratio (SNR) of about 20 dB and a broad bandwidth of about 500 MHz. Therefore, it is theoretically feasible to detect a single Co nanoparticle of about 10 nm size in a narrower bandwidth or with lock-in detection. By narrowing the noise bandwidth, sufficient SNR is achieved even for single nanoparticle detection.

As a proof of concept, a prototype spin valve detector and detector arrays were prepared with a sensor width of about 1 μm or less (along the direction normal to the sense current through the spin valve and to spin valve thickness). It has been demonstrated that, after applying a diluted drop of 11-nm diameter Co nanoparticle dispersion on such detectors, we can obtain a signal amplitude of greater than 1 mV (peak-to-peak) from a 1 μm wide spin valve detector (Li, G., et al., *Journal of Applied Physics*, Vol. 93, no 10 (2003), p. 7557). The sensitivity of the spin valve detector depends not only on the magnetization and volume of magnetic tags and their distance from the free layer of the spin valve, but also on the geometry and bias field of the spin valve itself. We have found that narrower spin valves generally lead to a higher sensitivity. Consequently, spin valve detectors and detector arrays suitable for use with the present invention have sensor widths from about 0.01 μm to about 1 μm along the direction normal to the sense current and to spin valve thickness.

We have performed micromagnetic and analytical simulations of various spin valve designs extensively and summarize the signal (peak-to-peak amplitude prior to any preamplifier) due to a single Co nanoparticle versus spin valve free layer width in Table 2. Both the in-plane and vertical modes of operation (FIG. 2B) are listed. The distance from the particle edge to the midplane of the free layer is assumed to be 6 nm. The free layer strip is 2 nm thick and 3 μm long, but its active length (not covered by leads) is 1 μm. The sense current density is taken to be $10^8$ A/cm$^2$, which is below the electromigration limit of the spin valve detector. The total detector thickness is about 34 nm. The magnetic moment of superparamagnetic Co nanoparticles have been calculated with the Langevin function.

We should have a sufficient signal level to detect a single 11-nm-diameter Co nanoparticle if the spin valve is made to be 0.2 μm wide and operated in the in-plane mode. Additionally, we can increase magnetic signal strength further by using FeCo-based magnetic nanotags, since the signal voltage is proportional to the magnetic moment in the tag.

TABLE 2

Spin valve signal voltage (peak-to-peak amplitude) versus free layer width. The voltage is due to a single Co nanoparticle with a diameter of 11 nm and its edge is 6 nm away from the midplane of the spin valve free layer. Both in-plane and vertical mode are listed, along with the relevant bias field and tickling field amplitudes.

|  |  | Free layer width | | |
|---|---|---|---|---|
|  |  | 1 μm | 0.2 μm | 0.2 μm |
|  | Sense current | 10 mA | 2 mA | 2 mA |
| In-plane mode | (bias field, tickling field) signal voltage | (100 Oe, 50 Oe) 0.32 μV | (100 Oe, 50 Oe) 2.1 μV | (100 Oe, 141 Oe) 4.9 μV |
| Vertical mode | (bias field, tickling field) signal voltage | (50 Oe, 50 Oe) 0.08 μV | (50 Oe, 50 Oe) 0.2 μV | (100 Oe, 141 Oe) 0.8 μV |

Electromagnetic Interference (EMI) Signal Rejection

Spin valve detection is typically performed with the in-plane mode (Li, et al., *J. Appl. Phys.* Vol. 93 (10): 7557 (2003)). The vertical mode, even though giving a slightly smaller signal amplitude, is extremely advantageous when the electromagnetic interference (EMI) signal due to the AC tickling field in the detection system is significant. The EMI signal tends to center at the frequency f of the AC tickling field, so it can be eliminated or greatly reduced if we perform lock-in detection at the frequency 2f. Furthermore, we can adopt a 2-bridge circuit to eliminate any remaining EMI.

Ultrathin Passivation of Detectors

The signal from the spin valve detector due to the magnetic tag depends on the distance between the magnetic tags and the free layer of the spin valve, in addition to the geometry and bias field of the spin valve itself. The detector voltage signal from a single Co particle decreases with increasing distance from the center of the particle to the midplane of the spin valve free layer.

As the sensing magnetic field from a magnetic particle drops monotonically with the distance between the sensor and the particle, it is preferred to make the free layer in the spin valves on top of the pinned layer. Furthermore, it is of utmost importance to minimize the distance between the magnetic particle and the top surface of the free layer, including the thickness of the passivation layer protecting the spin valves. However, during operation of the detector array, a solution of DNA will be flowed over the sensor surface to allow for hybridization of corresponding DNA fragments. Therefore, corrosion of the sensor surface is of major concern. Any degradation of the detector surface could sacrifice sensitivity by reducing the signal from hybridization events or by destroying the detectors altogether.

The magnetic detection schemes in the prior art have recognized this potentially catastrophic problem and consequently have added relatively thick passivation layers to their detector surfaces. If a conventional passivation layer is used, there would be a distance of greater than 1000 nm between center of the magnetic particle and the detector surface, greatly limiting the detector sensitivity. A trade-off occurs between retaining high sensitivity while sufficiently guarding against degradation. The MagArray™ detector design combines an ultrathin (less than 10 nm) layer of passivation and very small magnetic nanoparticle tags (diameter of about 20 nm or smaller), thus achieving a particle-center-to-detector distance of less than about 30 nm (including the intervening DNA fragment length of about 10 nm), which is close enough to provide the necessary sensitivity for single-tag detection. In accordance with the present disclosure, the ultrathin layers of passivation (such as Ta or Au) suitable for use with detectors such as the MagArray™ detector typically can have a thickness from about 1 nm to about 10 mm, allowing for achievement of particle-center-to-detector distances from about 6 nm to about 30 nm.

High Sensitivity MTJ Detectors

A MTJ detector is constructed similarly to a spin valve detector except that the non-magnetic spacer is replaced with a thin insulating tunnel barrier such as alumina and that the sense current flows perpendicular to the film plane. Electron tunneling between two ferromagnetic electrodes is controlled by the relative magnetization of the two ferromagnetic electrodes, i.e., tunneling current is high when they are parallel and low when antiparallel. A typical MTJ detector is composed of a bottom electrode, magnetic multilayers including a tunnel barrier, and a top electrode. MTJ detectors have magnetoresistance ratios as high as 50% and inherently large device resistances, yielding higher output voltage signals.

Conventional MTJ devices employ relatively thick (greater than 0.2 μm) top electrodes (Parkin, S. S. S. P., et al., *J. Appl. Phys.* 85: 5828 (1999)) that will greatly reduce the detected signal from a single magnetic nanoparticle, thus they are not suitable for the MagArray™ detector. To overcome this problem, we devised a double-layer top electrode. The first layer can be a thin gold layer (about 10 nm or less). Gold is desirable due to its ease for binding DNA probes. The second layer can be aluminum, copper or other conductive metals which do not bind with DNA probes, including palladium, palladium alloys, palladium oxides, platinum, platinum alloys, platinum oxides, ruthenium, ruthenium alloys, ruthenium oxides, silver, silver alloys, silver oxides, tin, tin alloys, tin oxides, titanium, titanium alloys, titanium oxides, and combinations thereof. An aperture in the second layer, slightly smaller in size than the MTJ, is created either by a lift-off process or by etching a uniform second layer. This design allows us to keep the distance between the nanoparticle tag and the top surface of the free magnetic layer very small, from about 6 nm to about 30 nm. Furthermore, this could circumvent current crowding (van de Veerdonk, R. J. M., et al., *Appl. Phys. Lett.*, 71: 2839 (1997)) within the top electrode which would likely occur if only a very thin gold electrode were used.

Except that the sense current flows perpendicular to the film plane, the MTJ detector can operate similarly to the spin valve detector, either with in-plane mode or vertical mode. The disclosure on EMI rejection and ultrathin passivation also applies to MTJ detectors, but to the advantage of MTJ detectors, the first top electrode of thin gold on MTJ also serves the triple purposes of electrical conduction, ultrathin passivation as well as specific DNA probe attachment.

At the same detector width and particle-detector distance, MTJ detectors give appreciably larger signals than spin valve detectors. For example, for an MTJ detector with a junction area of 0.2 μm by 0.2 μm and resistance-area product of 1 kOhm-μm$^2$, operating with a MR of 25% at a bias voltage of 250 mV, and $H_b$=35 Oe, $H_t$=100 Oe rms, the voltage signal from a single 11 nm diameter Co nanoparticle whose center is 35 nm away from the free layer midplane is about 20 μV, roughly an order of magnitude larger than those listed in Table 1 for similar-sized spin valve detectors. This is a great advantage for MTJ detectors over spin valve detectors. In accordance with the present invention, MTJ detectors suitable for use in practicing the invention can have junction areas from about 0.01 μm$^2$ to about 10 μm$^2$, and resistance area products from about 0.1 kOhm-μm$^2$ to about 100 kOhm-μm$^2$.

DNA Quantification and Dynamic Range

Single-tag detection has been previously demonstrated both experimentally (Li, G., et al., *Journal of Applied Physics*, Vol. 93, no 10 (2003), p. 755.7) and theoretically (Li, G., et al., *IEEE Trans. MAG*, Vol. 39, no. 5 (2003), p. 3313) in prototype MagArray™ detectors. In real applications, however, multiple particles may be on a detector, and their locations are likely not at the center of the detector surface. We found that the voltage signal from a single particle strongly depends on its lateral location on the detector surface, more so in the hard-axis direction (y-axis in FIG. 2A) of the free layer than in the easy-axis (x-axis in FIG. 2A). The calculated time-domain voltage signal under a sinusoidal tickling field versus the y-axis of an 11 nm diameter Co nanoparticle whose center is 25 nm away (z-axis in FIG. 2A) from the top surface of the free layer can be measured. The 2f signal gets distorted near the sensor edge and drops rapidly at the edge. Note that the overall detector signal is larger at the detector edge, but it consists of mostly 1f components which are out of phase at the two edges.

In order to count the magnetic nanoparticles quantitatively based on the amplitude of the voltage signal, we want each particle to generate the same signal regardless of its location. A spin valve detector may not allow us to quantify the number of particles accurately. The MagArray™ detector adopts a detection window which removes the nonuniformity near the edge. Note that the two-layer top electrode designs for MTJ can remove the edge uniformity as long as we make the Au window sufficiently smaller than the active junction. Depending on the detector geometry and the tolerance to signal variations, coverage of about 50% of active detector area may be desired.

The detection window described above allows the MagArray™ detector to count multiple nanoparticles (NP) very well. Based on the assumptions of equivalent averaged magnetic field of NPs and coherent magnetization rotation of the free layer, we have calculated the detector signals of multiple magnetic NPs uniformly or randomly distributed over a rectangular area somewhat smaller than the active detector area. For example, for a 4×0.3 μm$^2$ spin valve (SV) detector, the normalized signals of uniform NP arrays versus the actual NP numbers for different array aspect ratios can be determined. At low particle numbers the signal is fairly linear, and only at high particle numbers does the signal linearity degrade. A higher aspect ratio gives better signal linearity because more NPs are away from the sensor edges. The mean values and standard deviations of the normalized signals for randomly distributed NPs can be determined, which also indicates good signal linearity. We have done experiments on a monolayer of 16-nm $Fe_3O_4$ NPs coated on 0.3-μm wide SV sensors to verify the model.

These results indicate that the detector can not only detect 1-10 NPs but also count hundreds of NPs with a resolution of a few NPs, far exceeding the detection limit of state of the art optical microarrays. Furthermore, we could multiplex a set of detectors with various sensor widths and lengths such that the smaller detectors can sense low concentration biomolecules while the larger ones can sense and count high concentration biomolecules.

Nucleic Acid Probes Attached to Detector

An additional embodiment of the invention is directed towards nucleic acid probes (e.g. DNA or RNA) attached to a detector.

An oligonucleotide probe (binding molecule) complementary to the DNA fragment of interest (target molecule) is attached to the surface directly above the detector via a 5' linkage. To this end, the surface of the detector may be coated with a thin layer of glass or gold, and probe DNA may be attached. The attachment of probe DNA to glass surfaces via poly-L-lysine or to gold surfaces via a thiol linkage is widely practiced in biochemistry. Alternatively, a monolayer of self-assembled probe DNA can be prepared directly on the surface of the detector with no additional fabricated layer between the detector and the probe DNA.

The 5' end of the target DNA is labeled with a magnetic nanotag. During the hybridization step, the magnetically labeled target DNA attaches specifically to the immobilized probe DNA on the surface of the detector. It is highly preferred that the distance between magnetic tag and the free layer in the detector be kept to a minimum, since strength of the magnetic signal will be compromised if the distance between the detector and the signal is too great. One scheme is to apply an external magnetic field gradient during the hybridization step to concentrate target DNA and to pull the magnetic tag closer to the detector surface after the hybridization step. The external magnetic field may also be used to remove non-hybridized tagged DNA fragments.

Array Architecture

We have designed an architecture for the MagArray™ detector that is suitable for quantitative detection of DNA fragments. To utilize the substrate area efficiently, we have employed a scheme that appears similar to magnetic random access memory (MRAM), but in fact the MagArray™ detector is distinctively different from MRAM in that the MagArray™ detector does not require conduction lines for write currents and that the signal levels in the MagArray™ detector are much smaller. The cells in the MagArray™ detector need to share preamplifiers and a lock-in amplifier (or a narrow-band pass filter) so that signals as small as about 1 μV can be reliably detected. Each detector is connected to the drain of a switching transistor and each cell framed by one row conduction line (word line) and one column conduction line. We can read an individual detector by turning on the corresponding transistor and passing a sense current through the detector. The voltage change in the column lines are detected by the preamplifier and the lock-in amplifier.

A typical block with 1024 cells in the MagArray™ detector has been designed. Each block consists of a row decoder, a column decoder, a preamplifier, current sources, and an array of cells. At least one column of cells are covered with thick polymers, rendering them insensitive to magnetic nanoparticles, and thus can be used as reference detectors in a bridge circuit or a subtraction circuit. We estimate that the MagArray™ detector can have a density of as high as about $10^6$ cells/cm$^2$ (one detector per cell).

The DNA probes can be immobilized on the MagArray™ detector chips by conventional spotting or ink-jet printing. Each circular feature of DNA probes (or binding molecules) spans over a multiplicity of cells, but the probes bind only to the active detector area of each sensor within the feature. There is at least one feature per DNA probe to capture a corresponding DNA target. Unspecifically bound probes are then washed away without cross contamination. After hybridization with magnetically tagged DNA target samples, each detector within the same DNA feature will be interrogated individually, the resulting average signal is used to identify and quantify the DNA target captured by the DNA probes at a given site. In spite of the high density of chemically active sensor surfaces, they still occupy only a fraction of the cell area because a detector is much smaller than a cell.

Alternatively, to improve the chemical sensitivity of the MagArray™ detector, we have integrated microfluidic circuits directly onto the detector array so that DNA probes and target samples are only attached or directed at the detector surfaces which are sensitive to magnetic tags. Here we may achieve one detector (instead of one feature) per DNA probe, maximizing the number of different DNA probes which can be accommodated on a chip. Several methods exist to attach DNA probes specifically to surfaces such as silicon dioxide or gold which are selectively deposited on active detector surfaces only. This approach will greatly boost the overall chemical sensitivity, allowing us to detect minute amount of biomolecules, e.g., 1-10 target DNA fragments, to minimize the amount of DNA probes spotted on the MagArray™ detector, and to speed up the detection process.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Detection of Magnetite Nanoparticles

Figure 3A:
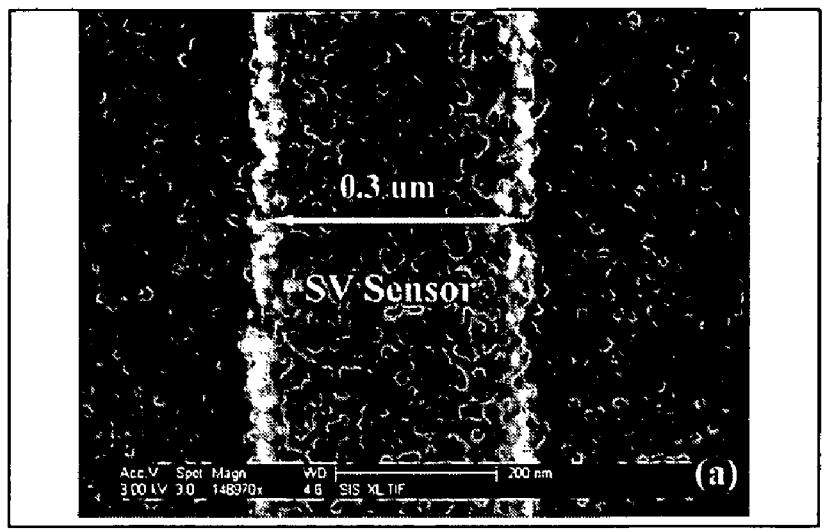
FIG. 3A illustrates a magnified view of a 16-nm $Fe_3O_4$ nanoparticle monolayer on a 0.3-µm spin valve (SV) sensor.
Figure 3B:
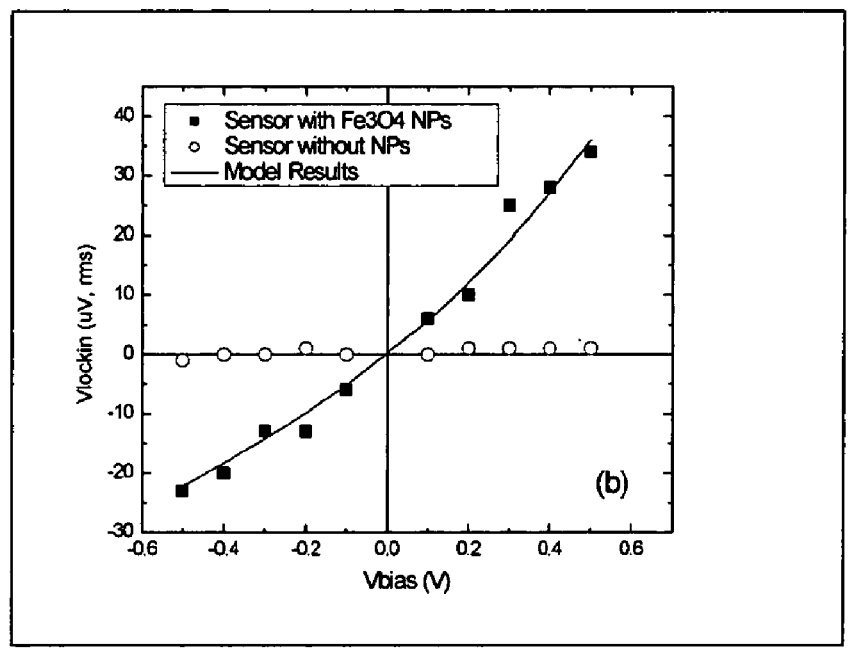
FIG. 3B illustrates a graph of the voltage signals of a 0.3-µm spin valve (SV) sensor with a $Fe_3O_4$ nanoparticle monolayer and a sensor without nanoparticles; the line is the modeling result.

A series of experiments was carried out to demonstrate that in addition to Co, Fe, and their alloys, ferrite such as magnetite and Mn-ferrite can also serve as biological tags, in accordance with the present invention. A monolayer of 16-nm $Fe_3O_4$ nanoparticles (NP) on 0.3-μm wide spin valve sensors was coated using polyethylenimine (PEI)-mediated self-assembly method (see, S. Sun, et al., *J. Am. Chem. Soc.*, 124, 2884 (2002)), as shown in FIG. 3A. It was found that the voltage signal from a spin valve covered magnetite nanoparticles are nearly proportional to the bias voltage applied to the sensor as expected, shown in FIG. 3B, while the signal from a reference spin valve not covered with any magnetite nanoparticles is nearly zero. The voltage signals were measured from a Wheatstone bridge circuit by a lock-in amplifier at different bridge circuit biases. Furthermore, it is demonstrated that the measured signals could be well described by an analytical model, such as described by G. X. Li and S. X. Wang in *IEEE Trans. Magn.*, 39 (5), 3313-5, (2003).

The detection of hundreds of magnetite nanoparticles in a patterned monolayer by a spin valve sensor was also demonstrated. It was found, using an experiment similar to that described above, that the maximum resistance change of the spin valve due to about 630 magnetite particles self assembled at the top surface of the spin valve was about 1.3Ω. In other words, the signal per particle was roughly 2 mΩ, which is equivalent to 2 μV of signal voltage if the sense current is 1 mA. The detection limit in this experiment was approximately 55 mΩ, suggesting that the minimum detectable number of the magnetite nanoparticles is about 30. However, it seems apparent that with a more sensitive sensor, such as magnetic tunnelling junctions and higher moment nanoparticles such as FeCo, an even lower detection limit of nanoparticles is reachable. Consequently, it is readily evident from this example that it is realistic to detect from tens of magnetic nanoparticles to single magnetic nanoparticles.

Example 2

Spin Valve Sensors with Ultrathin Passivation

The reliability of a 4 nm passivation layer has been studied through a series of passive corrosion studies. A prototype MagArray™ chip was submerged into one of two DNA solutions that are currently used in standard DNA microarrays. The first solution, a hybridization buffer (pH=7.5), consists of a mixture of 0.6 M NaCl, 0.06 M $C_6H_5Na_3O_7$ (sodium citrate), and 0.1% SDS (sodium dodecyl sulfate). As its name indicates, this solution is the primary medium for the actual hybridization step in the microarray. The other solution, a blocking solution (pH=7.9), is a proprietary product from Surmodics (Eden Prairie, Minn.), primarily used to remove nonspecific binding sites in the test area. This process increases the likelihood of target molecules interacting with probes. The final addition to these solutions was the DNA (sonicated salmon sperm DNA) at a concentration of 0.1 mg/mL.

The performance of the spin valve sensor after DNA solution exposures was evaluated by measuring its magnetoresistance (MR) ratio, $\Delta R/R_o$. This parameter was tracked over time in solution. The first step of the experiment was to locate an active spin valve sensor (width of about 300 nm) with an MR ratio that was reasonably high, about 6-7%. The MR ratio was measured by use of a probe station setup that gave resistance data with respect to applied field. The chip was placed in contact with a selected DNA solution for repeated 30 minute cycles after which the chip was removed, washed with deionized water, air dried, and measured for MR. After 2 hours of cycling, the chip was left in solution for a total of 24 hours and tested a final time. Note that the sensor currents were turned off when the detectors were in the solutions because hybridization and signal detection could be done sequentially.

Figure 4:
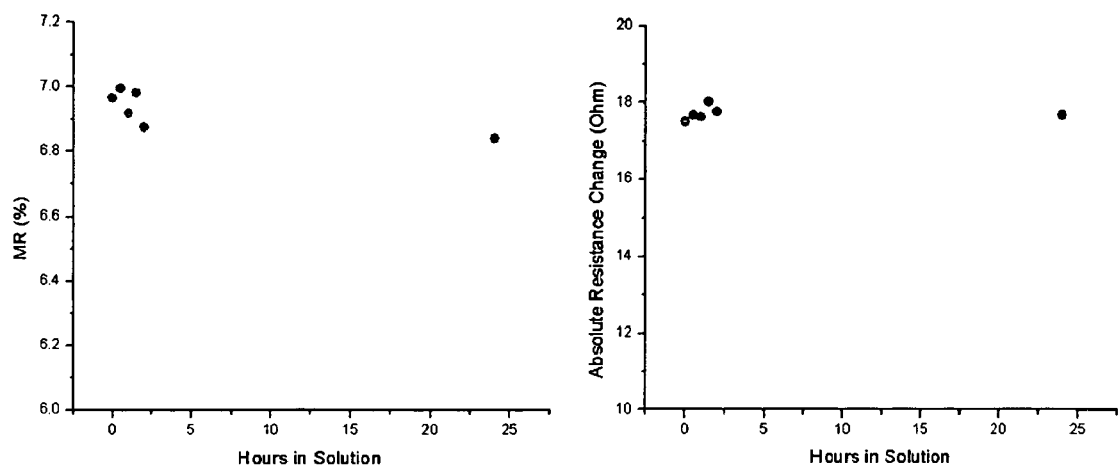
FIG. 4 shows the magnetoresistance (MR) and $\Delta R$ values for a spin valve sensor submerged in a blocking solution. As shown, the spin valve maintains its MR ratio and $\Delta R$ after 24 hours of exposure to the blocking solution.

The testing results for the blocking solution are shown in FIG. 4. All of the MR values lie between 6-7% with the highest deviation from the $0^{th}$ hour test being around 0.15%. The $\Delta R$ values deviate about $\pm 1\Omega$ from the $0^{th}$ hour value. Similarly, the results for the chip in hybridization solution show no dramatic difference from the blocking solution. The distribution of values is a bit wider for both MR and $\Delta R$. The MR varies no more than 0.4% from the $0^{th}$ hour and the $\Delta R$ scatter is within $4\Omega$. Thus, the spin valve sensor maintains reasonable levels for MR and $\Delta R$ through all hours of testing. These results support the MagArray™ design strategy of using ultrathin passivation layer.

Example 3

Synthetic Ferrimagnetic Nanoparticles

Figure 5:
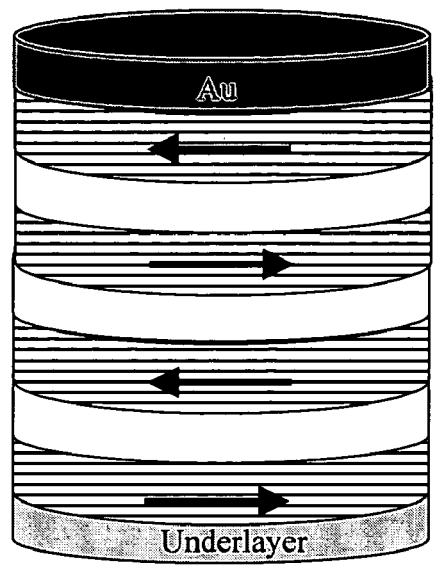
FIG. 5 shows a schematic representation of a synthetic antiferromagnetically coupled magnetic nanoparticle with an under layer (Underlayer) and a gold cap, Au. The layers with arrows are ferromagnetic layers which are antiferromagnetically coupled in the remanence state. The number of the ferromagnetic layers can vary from about 2 to about 6 depending upon the application. The gold cap is for bioconjugation, while the under layer is for proper film growth as well as biochemistry applications.

Here we disclose novel magnetic nanoparticle tags that are fabricated by physical methods instead of chemical routes and are suitable for labeling the target biomolecules to be detected in MagArray™. The tags consist of at least two thin ferromagnetic layers, preferably $Fe_xCo_{1-x}$, $0.5 \leq x \leq 0.7$, or $Fe_xCo_{1-x}$ based alloys. It is well known that $Fe_xCo_{1-x}$ has the highest saturation magnetization (about 24.5 kGauss) among the known ferromagnetic materials (Bozorth, R. M., *Ferromagnetism*, D. Van Nostrand Company, 1951). These ferromagnetic layers are separated by nonmagnetic spacer layers such as Ru, Cr, Au, etc., or their alloys. The spacer layers are appropriately engineered to make the ferromagnetic layers coupled antiferromagnetically so that the net remnant magnetization of the resulting particles are zero or near zero, as shown in FIG. 5. A gold cap is added at the top of the antiferromagnetic stack so that the nanoparticle can be conjugated to biomolecules via the gold-thiol linkage or other chemical bonding. The edge of the nanoparticles can be passivated for chemical stability with Au or other thin inert layers. Many physical methods can be conceived by those familiar with the art to fabricate the nanoparticles described above.

Example 4

Additive Fabrication Method of Synthetic Ferrimagnetic Nanoparticles

Figure 6:
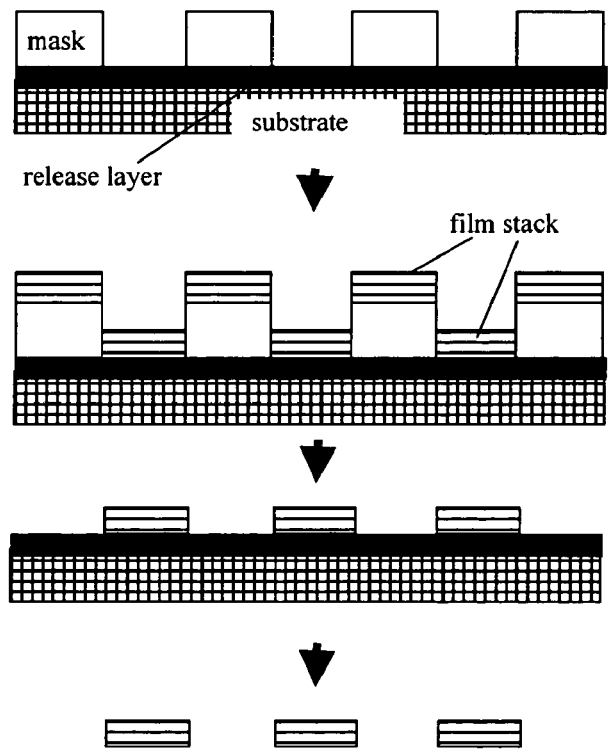
FIG. 6 illustrates an additive fabrication method of synthetic ferromagnetic nanoparticles.

An additive fabrication method is shown in FIG. 6. As shown therein, going from the top of the figure to the bottom in the direction of the arrows, the fabrication method begins with the deposition of a continuous thin layer (for releasing particles later) on an ultrasmooth substrate, then depositing a mask layer on the release layer. Finally, identical holes are patterned into the mask layer.

In the next step, the film stack is deposited on the mask layer. The film stack, similar to that shown in FIG. 5, includes the ferromagnetic layers, spacer layers, and the gold cap. Following the deposition, the mask layer is removed, lifting off the unwanted films deposited on the mask layer. Finally, the release layer is removed, lifting off the magnetic nanoparticles into a solution which can then be used as magnetic tags.

Example 5

Integration of Microfluidic Channels with Detectors

Figures 7A, 7B:
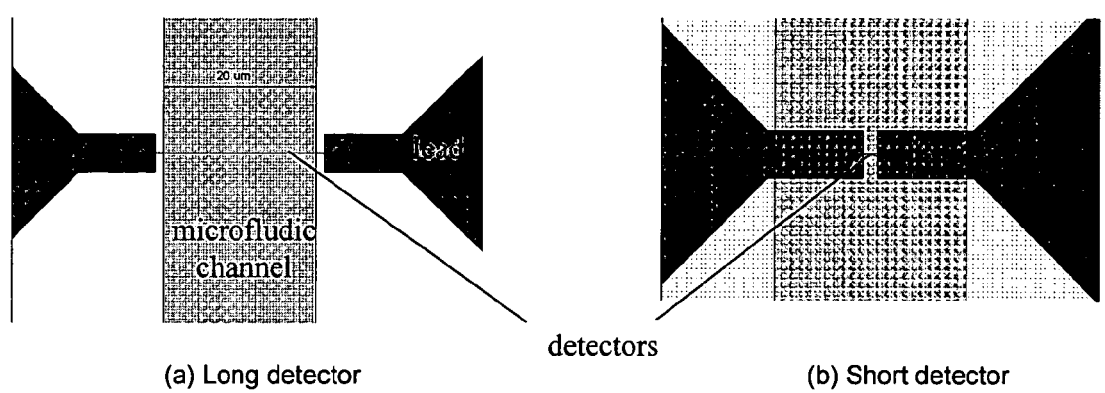
FIG. 7A shows microfluidic channels directly integrated on a long detector, with the DNA probes attached specifically to the detector surface. As shown in the figure, the detector is made slightly larger than 20 µm, the width of the microfluidic channel, while the long detector is suitable for relatively large quantities of DNA samples.
FIG. 7B shows microfluidic channels directly integrated on a short detector, with the DNA probes attached specifically to the detector surface. The detector is made shorter than the width of the microfluidic channel, so as to be more suitable for use with relatively small quantities of DNA samples.

In order to improve the chemical sensitivity of the MagArray™, we have integrated microfluidic circuits (Thorsen, T., et al., *Science*, Vol. 298, p. 580 (2002)) directly on the detector array so that DNA probes and target samples are only attached or directed at the detector surfaces which are sensitive to magnetic tags, thereby minimizing waste of DNA probes or DNA targets. The schematic of such systems are shown in FIGS. 7A and 7B. The DNA probes are attached specifically to detector surface. In FIG. 7A, the detector is made slightly longer than 20 μm which is the width of microfluidic channel. The long detector is suitable for relatively large quantities of DNA samples. In FIG. 7B, the detector is made shorter than the width of the microfluidic channel. The short detector is more suitable for relatively small quantities of DNA samples. In the latter case, applied electric field or magnetic field gradient, and hydrodynamic focusing schemes can be used to direct the DNA samples to the detector surface. It is also conceivable to make the microfluidic channel in FIG. 7B as wide as the detector length.

All of the compositions and/or methods and/or processes and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. A magnetic tunnel junction detector array, said array comprising:
   a plurality of detection sites, wherein each detection site of said plurality comprises:
   a magnetic tunnel junction detector comprising:
      a bottom electrode;
      a tunnel barrier layer; and
      a double-layer top electrode comprising:
         a first thin layer, wherein said first thin layer is from about 1 nm to about 10 nm in thickness; and
         a second layer contacting said first layer, wherein said second layer is a conductive layer and comprises an aperture exposing a part of said first layer,
      wherein said tunnel barrier layer is disposed between bottom electrode and said double-layer top electrode; and
   a binding molecule covalently bonded to said magnetic tunnel junction detector.

2. The magnetic tunnel junction detector array according to claim 1 wherein said tunnel barrier layer comprises a plurality of magnetic layers contacting the bottom electrode; a tunnel barrier contacting at least one of the plurality of magnetic layers; and a ferromagnetic layer on the top of the tunnel barrier.

3. The magnetic tunnel junction detector array according to claim 1, wherein said first thin layer is a gold layer.

4. The magnetic tunnel junction detector array according to claim 1, wherein said conductive layer comprises a material selected from the group consisting of aluminum, copper, palladium, platinum, ruthenium, silver, tin, titanium, alloys thereof, oxides thereof, and combinations thereof.

5. The magnetic tunnel junction detector array according to claim 1 wherein said binding molecule is covalently bonded to said first thin layer exposed by said aperture.

6. The magnetic tunnel junction detector array according to claim 5, wherein said first thin layer is a gold layer.

7. The magnetic tunnel junction detector array according to claim 6 wherein said binding molecule is covalently bonded to said gold layer by a gold-thiol covalent bond.

8. The magnetic tunnel junction detector array according to claim 1 further comprising a row decoder, a column decoder, a preamplifier, and at least one current source.

9. The magnetic tunnel junction detector array according to claim 1 further comprising microfluidic circuits.

* * * * *

UNITED STATES PATENT AND TRADEMARK OFFICE
CERTIFICATE OF CORRECTION

| | | |
|---|---|---|
| PATENT NO. | : 7,682,838 B2 | Page 1 of 1 |
| APPLICATION NO. | : 11/938187 | |
| DATED | : March 23, 2010 | |
| INVENTOR(S) | : Wang et al. | |

It is certified that error appears in the above-identified patent and that said Letters Patent is hereby corrected as shown below:

• Please insert at Column 1, line 18:

-- FEDERALLY-SPONSORED RESEARCH OR DEVELOPMENT
This invention was made with Government support under contract N00014-02-1-0807 awarded by the Navy. The Government has certain rights in this invention. --

Signed and Sealed this
Twenty-fifth Day of December, 2012

David J. Kappos
*Director of the United States Patent and Trademark Office*